US00PP33532P2

(12) United States Plant Patent
Egger

(10) Patent No.: US PP33,532 P2
(45) Date of Patent: Sep. 28, 2021

(54) ***HEUCHERA* PLANT NAMED 'BLACK FOREST CAKE'**

(50) Latin Name: ***Heuchera* hybrid**
Varietal Denomination: Black Forest Cake

(71) Applicant: Terra Nova Nurseries, Inc., Canby, OR (US)

(72) Inventor: Janet N. Egger, Seattle, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 17/212,110

(22) Filed: Mar. 25, 2021

(51) Int. Cl.
*A01H 6/80* (2018.01)
*A01H 5/02* (2018.01)

(52) U.S. Cl.
USPC ..... Plt./440

(58) Field of Classification Search
USPC ..... Plt./440
See application file for complete search history.

*Primary Examiner* — Annette H Para
(74) *Attorney, Agent, or Firm* — Klarquist Sparkman, LLP

(57) ABSTRACT

A new and distinct *Heuchera* plant named is provided herein, characterized by dark chocolate brown leaf color, medium large leaves held on fairly short petioles, dark pink-red flowers on upright flowering stems, excellent performance in sun or shade, a medium, tall mounding habit with an excellent crown count, and excellent vigor.

2 Drawing Sheets

Botanical denomination: *Heuchera* hybrid.
Variety designation: 'Black Forest Cake'.

BACKGROUND OF THE INVENTION

The present invention relates to a new and distinct cultivar of *Heuchera* given the cultivar name of 'Black Forest Cake'. *Heuchera* is in the family Saxifragaceae. *Heuchera* 'Black Forest Cake' originated as a controlled cross using proprietary, unpatented, unnamed plant as both the seed and pollen parent. These parents are a result of breeding plan to produce dark leaved *Heuchera* with good floral display.

Compared to the seed parent, the new cultivar has larger, dark brown leaves with a slight glossy and a larger habit.

Compared to the pollen parent, the new cultivar has darker brown leaves, and a much larger red inflorescence and more crowns.

Compared to *Heuchera* 'Obsidian', U.S. Plant Pat. No. 14,836, the new cultivar has more undulate leaves that are more Chocolate-brown rather than black. *Heuchera* 'Black Forest Cake' has a larger habit and much improved floral display compared to 'Obsidian'

Compared to *Heuchera* 'Paris', U.S. Plant Pat. No. 18,881, the new cultivar has a larger habit and dark, semi glossy leaves and larger and more numerous inflorescence.

*Heuchera* 'Black Forest Cake' is uniquely distinguished by:

1. Dark chocolate brown leaf color,
2. Medium large leaves held on fairly short petioles,
3. Dark pink-red flowers on upright flowering stems,
4. Excellent performance in sun or shade,
5. A medium, tall mounding habit with an excellent crown count, and
6. Excellent vigor This new cultivar has been reproduced only by asexual propagation (tip cuttings and tissue culture using growing tips). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

DETAILED PLANT DESCRIPTION

Figure 1:
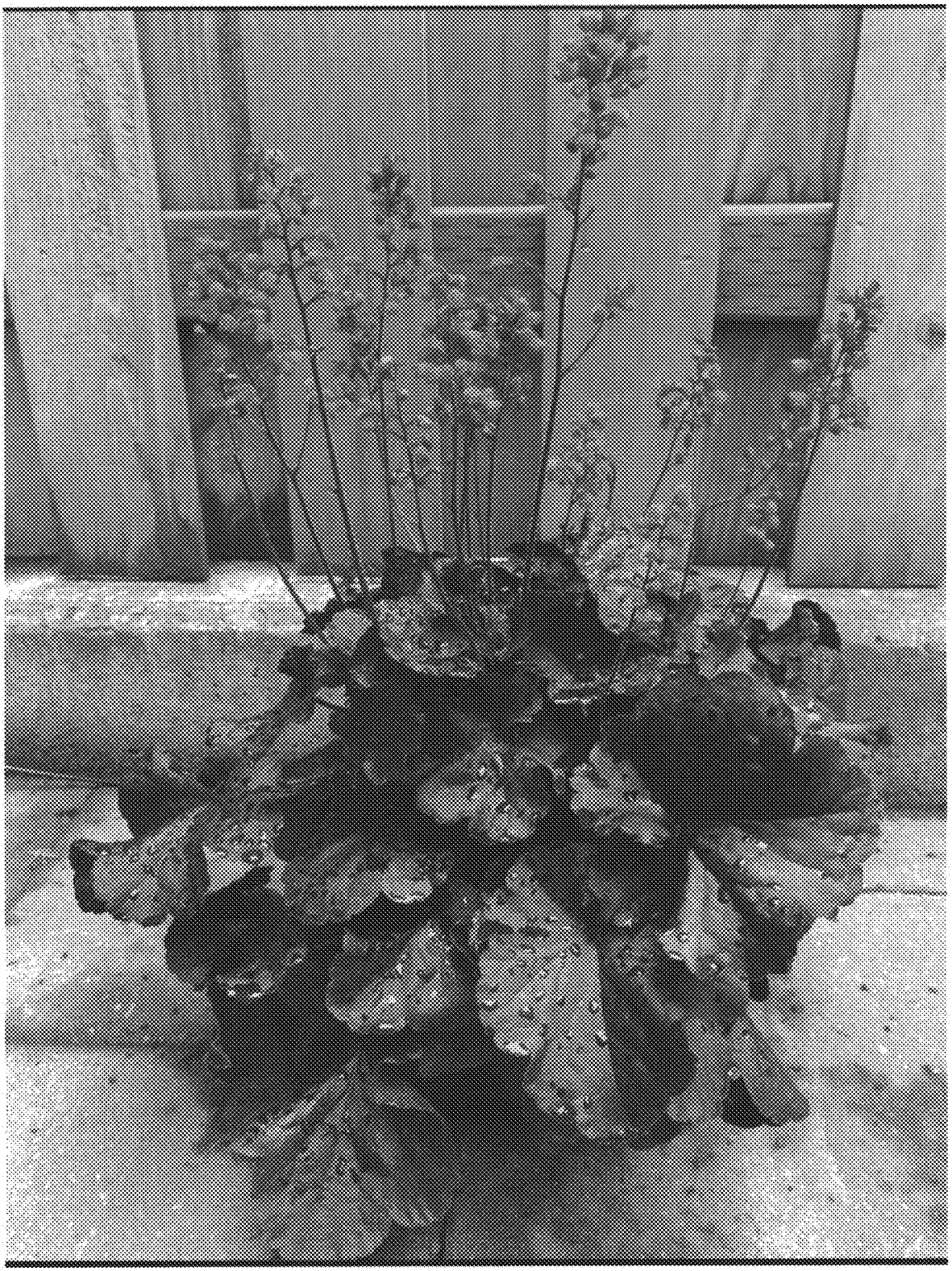
FIG. 1 shows a 10 month old *Heuchera* 'Black Forest Cake' in a one gallon container, grown outside in Canby, Oreg.
Figure 2:
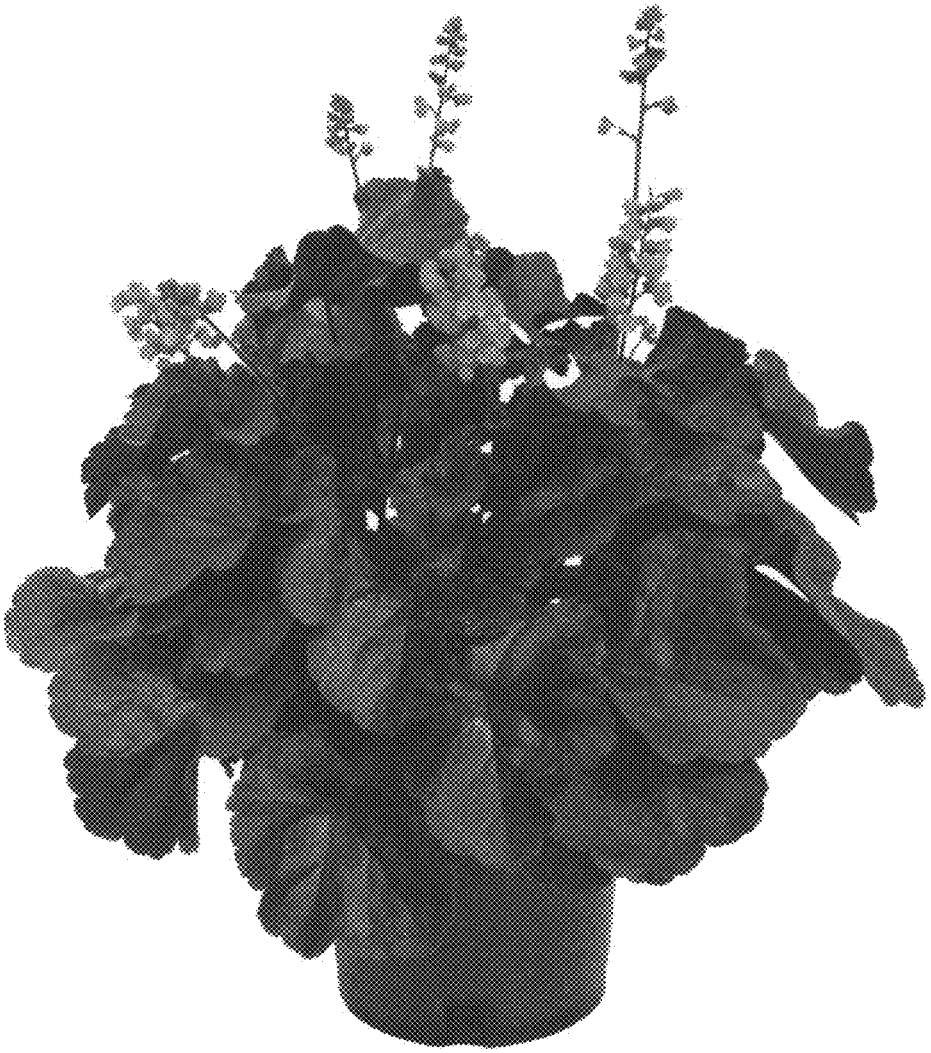
FIG. 2 shows a one gallon container of *Heuchera* 'Black Forest Cake' grown in a greenhouse setting.

The following is a detailed description of the new *Heuchera* cultivar based on observations taken in September of an eight-month-old specimen growing in a one-gallon pot in partial shade in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on *The Royal Horticultural Society Colour Chart,* 5$^{th}$ edition, 2007.

Plant:

*Form.*—Basal rosette, herbaceous perennial.
*Hardiness.*—USDA Zone 4 to 9.
*Size.*—35 cm tall from top of the foliage to the ground, 45 cm from ground to top. of flowers, 40 cm wide.
*Number of crowns.*—About 8.
*Habit.*—Large, mounding.
*Vigor.*—Excellent.

Leaf:

*Type*.—Simple.
*Arrangement*.—Rosette.
*Shape*.—Orbicular to ovate.
*Number*.—About 89.
*Blade size*.—Grows to 11 cm long and 11.5 cm wide.
*Venation*.—Palmate.
*Lobing/division*.—Palmately lobed with 6 main lobes with secondary lobes.
*Undulation*.—Moderate.
*Glossiness*.—Medium.
*Margins*.—Broadly crenate.
*Apex*.—Mucronulate.
*Base*.—Cordate, overlapping at sinus.
*Surface texture*.—Sparsely glandular-puberulent on both sides.
*Leaf rugosity*.—Medium.
*Petiole description*.—Grows to 16.5 cm long and 3 mm wide, glandular hairs, 187B.
*Leaf color*.—New leaves, topside closest to black 203B.

Inflorescence:

*Size*.—Grows to 5 cm wide and 9.5 cm long.
*Type*.—Upright thyrse.
*Number of flowers per thyrse*.—About 37.
*Flower density*.—Medium to dense.
*Number of thyrse*.—Up to 30.
*Peduncle*.—Grows to 30 cm long and 4 mm wide at base, glandular hairs, Greyed Purple N186C.
*Flowering stem attitude*.—Upright.
*Pedicel*.—Grows to 3 mm long, with glandular hairs, N186D.
*Bloom period*.—Late June through September in Canby, Oreg.

Flower bud:

*Size*.—4 mm wide and 3 mm long.
*Description*.—Glandular-puberulent, ovoid, facing outward.
*Color*.—Red Purple 61B.

Flower:

*Type*.—Perfect.
*Shape*.—Campanulate.
*Attitude*.—Outward, slightly downward-facing.
*Size*.—5 mm long and 9 mm wide.
*Corolla description*.—Campanulate, 2 mm long and 1 mm wide; 5 lobes each 1 mm wide and 2 mm long, oblong in shape, back side glandular-puberulent, glabrous inside, tip obtuse, margin entire, outside color Red-Purple 61C on both sides.
*Calyx description*.—Campanulate, 3 mm long and 2 mm wide, spatulate, margins entire, tip acute, glandular-puberulent on back side, glabrous inside, Red-Purple 60D on both sides, darkening to Red-Purple 60A at apex.
*Stamen description*.—5 in number, filaments 1.5 mm long, Red-Purple 65C, anthers 0.5 mm long, Greyed-Orange 169B, pollen plentiful, Greyed-Orange N67B.
*Pistil description*.—1, 2-beaked, 4 mm long and 2 mm wide, Red Purple 69A overall, ovary 2 mm long and 2 mm wide, style 2 mm long.
*Lastingness*.—Each thyrse blooms for about 3 weeks on the plant.

Fruit:

*Type*.—Two-beaked ovoid capsule.
*Fertility*.—Moderate.
*Color*.—Greyed Brown 199A.

Seed:

*Shape*.—Linear.
*Size*.—2 mm long.
*Color*.—Black 202A.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

* * * * *